United States Patent
Kato et al.

(10) Patent No.: US 12,096,954 B2
(45) Date of Patent: Sep. 24, 2024

(54) ENDOSCOPIC SURGICAL TOOL

(71) Applicant: OLYMPUS MEDICAL SYSTEMS CORP., Tokyo (JP)

(72) Inventors: Hiromasa Kato, Tokyo (JP); Yusuke Shiota, Machida (JP)

(73) Assignee: Olympus Medical Systems Corp., Tokyo (JP)

( * ) Notice: Subject to any disclaimer, the term of this patent is extended or adjusted under 35 U.S.C. 154(b) by 299 days.

(21) Appl. No.: 17/676,894

(22) Filed: Feb. 22, 2022

(65) Prior Publication Data

US 2022/0273329 A1 Sep. 1, 2022

Related U.S. Application Data

(60) Provisional application No. 63/154,380, filed on Feb. 26, 2021.

(51) Int. Cl.
*A61B 17/3205* (2006.01)
*A61B 17/00* (2006.01)

(52) U.S. Cl.
CPC .. *A61B 17/32053* (2013.01); *A61B 17/00234* (2013.01); *A61B 2017/00238* (2013.01); *A61B 2017/00323* (2013.01); *A61B 2017/00336* (2013.01); *A61B 2017/00929* (2013.01)

(58) Field of Classification Search
CPC ...... A61B 17/00234; A61B 17/320016; A61B 17/32053; A61B 18/082; A61B 18/10; A61B 18/1206; A61B 18/14; A61B 2017/00238; A61B 2017/00269; A61B 2017/00323; A61B 2017/00336; A61B 2017/00929; A61B 2018/00595;
(Continued)

(56) References Cited

U.S. PATENT DOCUMENTS

2020/0315437 A1* 10/2020 Yuasa .................. A61B 1/0125

FOREIGN PATENT DOCUMENTS

| JP | 2009-240380 A | 10/2009 |
| JP | 2019-500956 A | 1/2019 |
| WO | 2020/201823 A1 | 10/2020 |

OTHER PUBLICATIONS

Office Action dated Feb. 7, 2023, issued in corresponding Japanese Patent Application No. 2022-025827.

* cited by examiner

*Primary Examiner* — Mohamed G Gabr
(74) *Attorney, Agent, or Firm* — Morgan, Lewis & Bockius LLP

(57) ABSTRACT

An endoscopic surgical tool including a housing having a proximal end and a distal end, the housing having a central axis and a first aperture forming an opening disposed at the distal end, an insulator disposed within the housing and having a central bore and a second aperture, the insulator configured to extend distally from the first aperture along the central axis, and a knife disposed within the first aperture and including a tip. The knife having a retracted position and an extended position, wherein in the extended position, the knife is extended distally from the first aperture along the central axis and in the retracted position, the knife is retracted proximally towards the proximal end along the central axis. The endoscopic surgical tool including a biasing element coupled to the knife and biasing the knife toward the retracted position when the knife is in the extended position.

20 Claims, 13 Drawing Sheets

(58) Field of Classification Search
CPC .. A61B 2018/00601; A61B 2018/1425; A61B 2018/144; A61B 2090/08021
See application file for complete search history.

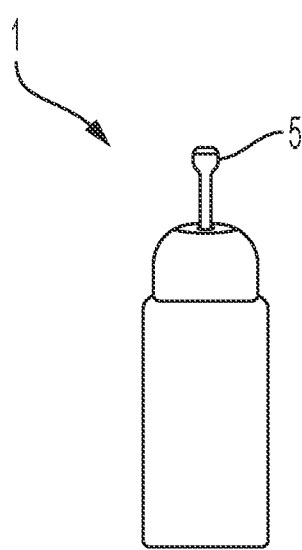
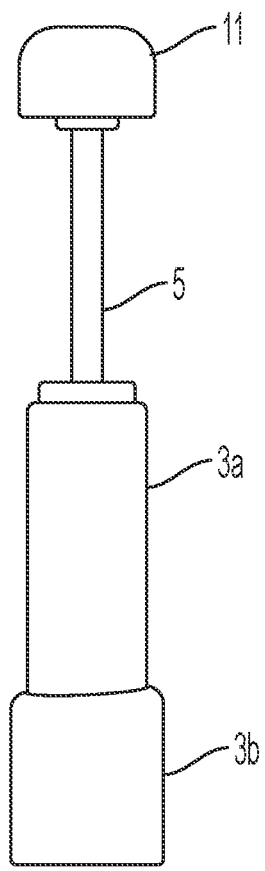
FIG. 2A
(PRIOR ART)
FIG. 2B
(PRIOR ART)

ENDOSCOPIC SURGICAL TOOL

CROSS-REFERENCE TO RELATED APPLICATION(S)

This application claims the benefit of and priority to U.S. Provisional Application No. 63/154,380, filed on Feb. 26, 2021, the entirety of which is incorporated by reference herein.

FIELD OF THE INVENTION

The present invention generally relates to an endoscopic surgical tool for use during endoscopic submucosal dissection and, more particularly, to an endoscopic surgical tool to remove tumors or tissue during an endoscopic submucosal dissection.

BACKGROUND OF THE INVENTION

Endoscopic submucosal dissections (ESDs) are procedures to remove tumors present in the gastrointestinal (GI) tract of a patient. Current procedures for removing tumors in the GI tract require the use of a needle-shaped knife or a knife with an insulator at the tip. However, switching between tools during surgery can be cumbersome and increase the length of the surgery including the time that the patient is under anesthesia. Further, existing knives may include one or more of a surgical instrument providing high frequency treatment free of an insulating tip, also referred to as a needle-shaped knife, and a surgical instrument providing high frequency treatment with an insulator at the tip, also referred to as a knife with an insulator at the tip. However, in use, the needle-shaped knife can protrude from the insulator of the knife causing perforation of the GI tract or bowels.

BRIEF DESCRIPTION OF THE SEVERAL VIEWS OF THE DRAWINGS

The following detailed description of embodiments of the endoscopic surgical tool, will be better understood when read in conjunction with the appended drawings of exemplary embodiments. It should be understood, however, that the invention is not limited to the precise arrangements and instrumentalities shown.

FIGS. 2A-2B are illustrations of a prior art endoscopic surgical tool.

DETAILED DESCRIPTION OF THE EXEMPLARY EMBODIMENTS OF THE INVENTION

Figure 1C:
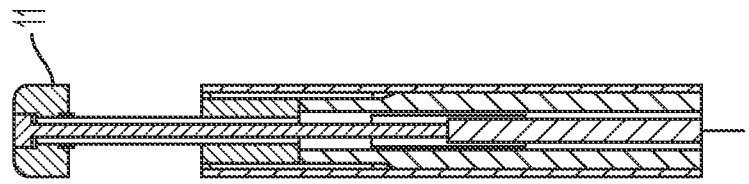
FIGS. 1A-1C are illustrations of a prior art endoscopic surgical tool.
Figure 1B:
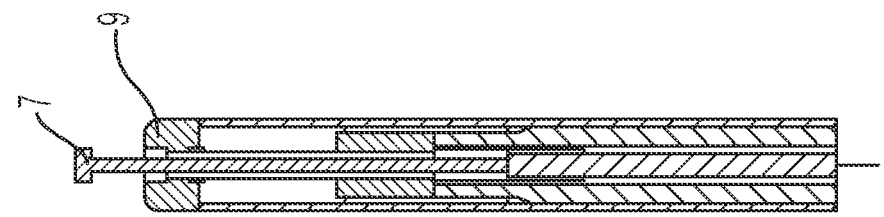
Figure 1A:
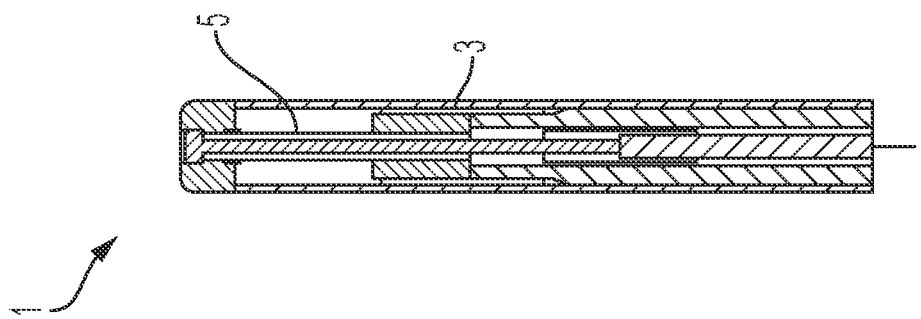

Referring to FIGS. 1A-2B, existing endoscopic surgical tools have been used to perform endoscopic submucosal dissections (ESDs) and remove tumors. As shown in FIGS. 1A-1C, a known endoscopic surgical tool 1 may include sheath 3, knife 5, and insulator 11. Insulator 11 includes aperture 9 and knife 5 may extend through aperture 9 of insulator 11. A user may use endoscopic surgical tool 1 in one of two configurations: needle-shaped knife configuration (FIGS. 1B and 2A) and knife with an insulator at the tip configuration (FIGS. 1C and 2B). For example, a user may use endoscopic surgical tool 1 in the needle-shaped knife configuration with knife 5 protruding through aperture 9 of insulator 11 and insulator 11 remaining within sheath 3. The needle-shaped knife configuration may be used for slow and careful procedures to allow for precise cuts and excisions. A user may use endoscopic surgical tool 1 in the knife with an insulator at the tip configuration with knife 5 and insulator 11 fully extended at the distal end of endoscopic surgical tool 1.

In some embodiments, tip 7 of knife 5 is disposed within insulator 11 and insulator 11 is used to prevent perforation of tissue by knife 5. The knife with an insulator at the tip configuration may be used for quick procedures. In practice, during, for example, quick dissections, use of knife 5 and/or tip 7 of endoscopic surgical tool 1 in the knife with an insulator at the tip configuration may inadvertently extend through insulator 11 causing accidental perforation of tissue or the GI tract. For example, when endoscopic surgical tool 1 is in the knife with an insulator at the tip configuration and is used hastily or for quick dissections, endoscopic surgical tool 1 may have an increased risk of perforating the GI tract compared to slowly using endoscopic surgical tool 1 in the knife with an insulator at the tip or needle-shaped knife configurations. Knife 5 may inadvertently extend through insulator 11 regardless of the movement of tip 7 and may cause perforation of tissue or the GI tract. Perforation of the GI tract can lead to severe pain, sepsis, internal bleeding, or other injuries.

Referring to FIGS. 2A-2B, endoscopic surgical tool 1 may include sheath 3. Sheath 3 may include inner layer 3a and outer layer 3b. Inner layer 3a may be disposed within outer layer 3b to provide protection to knife 5 and rigidity to endoscopic surgical tool 1. Inner layer 3a and outer layer 3b may also provide housing for internal wires and components of endoscopic surgical tool 1. In some embodiments, sheath 3 being comprised of two layers, inner layer 3a and outer layer 3b, results in endoscopic surgical tool 1 being substantially rigid, which prevents endoscopic surgical tool 1 from flexing and bending when passing through an endoscope disposed in an lumen, such as the GI tract. For example, sheath 3 being comprised of two layers, inner layer 3a and outer layer 3b results in endoscopic surgical tool 1 being stiff, thereby reducing and/or inhibiting the bending of the endoscope that endoscopic surgical tool 1 is inserted into.

Exemplary embodiments of the present invention provide an endoscopic surgical tool. Embodiments of the present invention provide an exemplary endoscopic surgical tool 200 as shown in FIGS. 3-9. In use, endoscopic surgical tool 200 may facilitate the removal of tumors disposed within the GI tract. Specifically, endoscopic surgical tool 200 may be used to cut and excise tumors that are located along the GI tract during procedures, such as ESD procedures. Endoscopic surgical tool 200 may include a needle-shaped knife configuration (FIG. 3) also known as a needle-sharp knife configuration, and a knife with insulator at the tip configuration (FIG. 5), also known as an insulated-tip knife configuration. For example, the needle-sharp knife configuration of FIG. 3 may be when the knife is extended, but the insulator is still disposed within the housing. In contrast, the knife with an insulator at the tip configuration of FIG. 5 may be when both the insulator and the knife are extended away from the housing and the tip of the knife is disposed within a recess of the insulator. The needle-shaped knife configuration may be used for slow and precise excision of tissue, such as a tumor, whereas the knife with an insulator at the tip configuration may be used for quick and sweeping removal of tissue or a tumor. For example, the needle-shaped knife configuration being devoid of the insulator in the extended position compared to the knife with an insulator at the tip configuration allows the operator or surgeon to view portions of tumor or tissue disposed along the GI tract that need to be peeled and excised. The needle-shaped knife configuration allows the operator or surgeon to slowly peel the tissue or tumor, which is crucial when hemorrhaging is expected, such as during ESD procedures.

In practice, when using endoscopic surgical tool 200 in the needle-shaped knife configuration, the operator or surgeon may proceed slowly to prevent inadvertent perforation of the GI tract by the knife. In contrast, the knife with an insulator at the tip configuration allows the operator or surgeon to quickly remove the tumor or tissue without concern for inadvertent perforation of the GI tract. For example, the insulator disposed at the distal end of the knife prevents the knife from inadvertently damaging the GI tract, allowing the operator or surgeon to perform the necessary procedures quickly.

Figure 3:
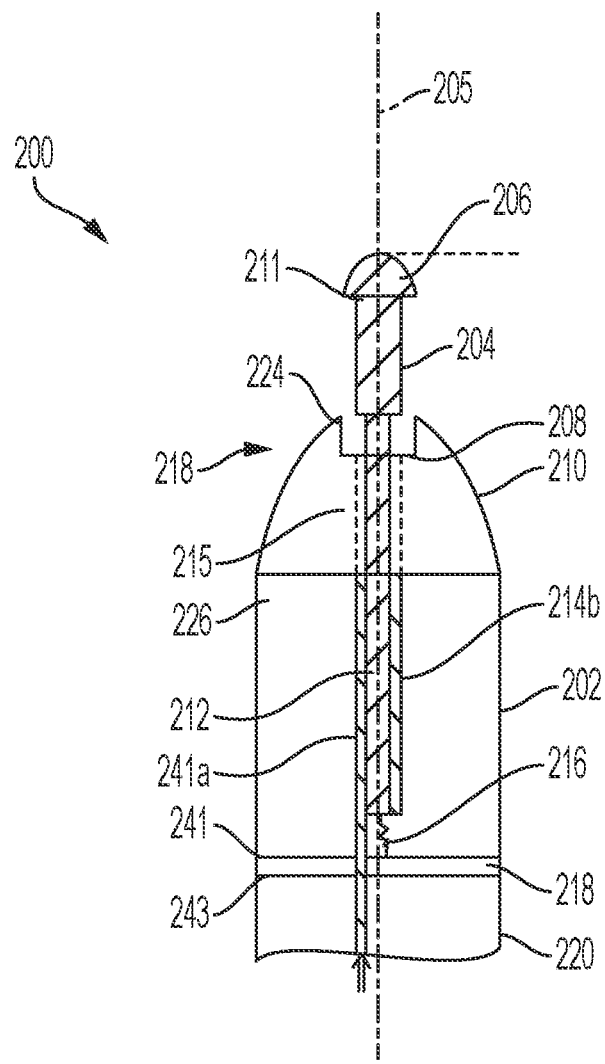
FIG. 3 is a cross-sectional view of an exemplary endoscopic surgical tool in accordance with an embodiment of the present invention shown in a retracted position.
Figure 4:
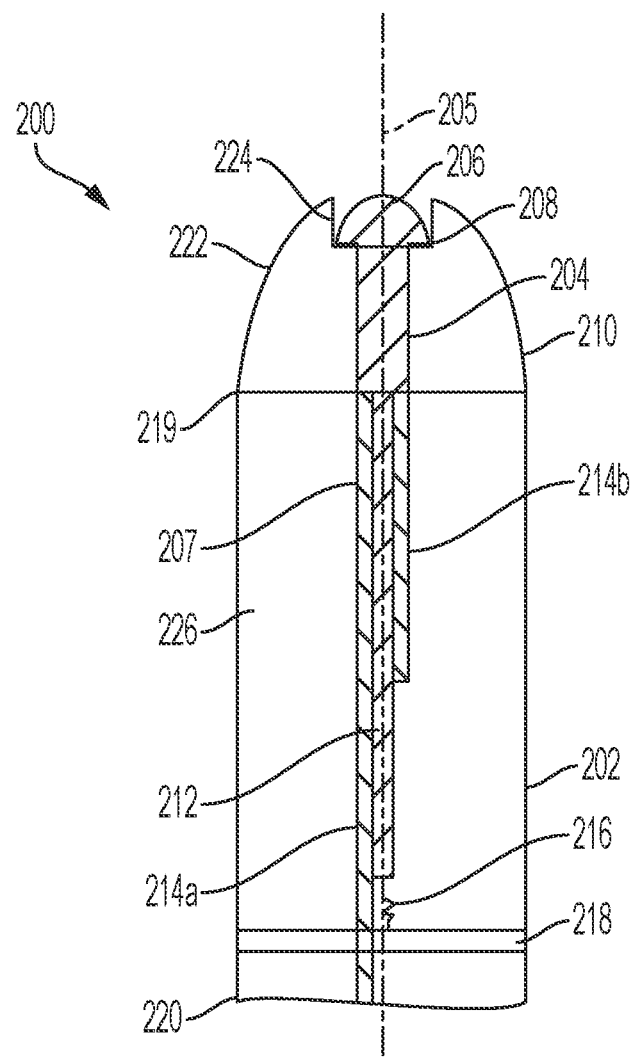
FIG. 4. is a cross-sectional view of the endoscopic surgical tool of FIG. 3 shown in a partially extended position.
Figure 5:
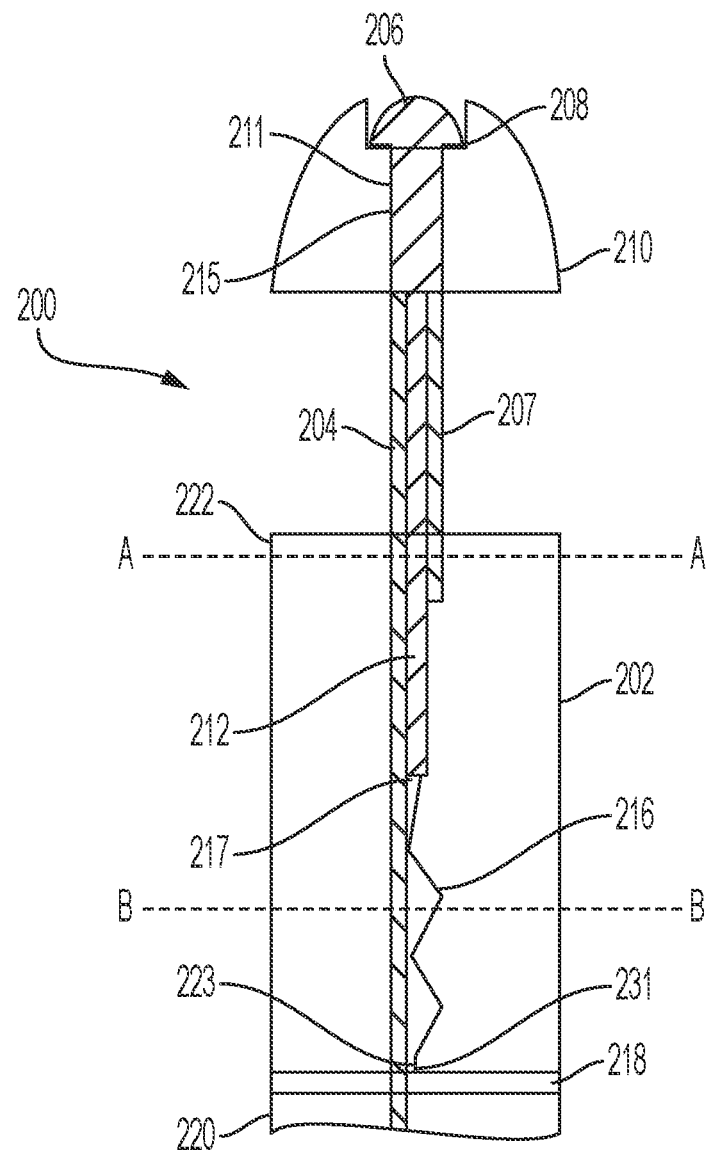
FIG. 5 is a cross-sectional view of the endoscopic surgical tool of FIG. 3 shown in an extended position.

As shown in FIGS. 3-5, endoscopic surgical tool 200 may include housing 202, knife 204, insulator 210, biasing element 216, and plate 218. Housing 202 may include an imaginary axis, central axis 205, extending along the center length of housing 202. Housing 202 may also include opening or aperture 219, proximal end 220, and distal end 222. Proximal end 220 may be disposed opposite distal end 222. Knife 204 may be disposed within housing 202 along central axis 205 and insulator 210 may be located adjacent a distal end of knife 204. Knife 204 may be disposed through insulator 210 and may include tip 206. Insulator 210 and knife 204 may be configured to extend distally away from housing 202 and opening 219 along central axis 205 and retract proximally towards housing 202 and opening 219 along central axis 205. In some embodiments, opening 219 is disposed at distal end 222 and plate 218 is disposed proximate proximal end 220.

In some embodiments, knife 204 may include rod 212, cutting surface 207, and distal portion 211. Knife 204 may include cutting edges 214a and 214b, which may surround rod 212. In some embodiments, cutting edges 214a and 214b comprise cutting surface 207. In some embodiments, knife 204, comprising distal portion 211 and cutting surface 207, is configured to cut and/or cauterize tissue. For example, distal portion 211 and cutting surface 207 may be configured to be heated or receive electrical current to cauterize tissue, may be comprised of blades or sharp edges to cut tissue, or may include lasers or other elements capable of cutting and/or cauterizing tissue. Cutting surface 207 may be configured to extend proximally from the proximal end of distal portion 211 and distal portion 211 may be disposed between tip 206 and cutting surface 207. For example, rod 212 and cutting edges 214a, 214b may extend proximally from the proximal end of distal portion 211. However, distal portion 211 may include rod 212 and/or cutting edges 214a, 214b. In one embodiment, distal portion 211 is comprised of a unitary cutting edge instead of rod 212 and cutting edges 214a, 214b. Knife 204 may be configured to extend along central axis 205 through insulator 210 via aperture 208. In some embodiments, insulator 210 is disposed within housing 202 and is configured to extend distally away from housing 202 along central axis 205. For example, insulator 210 may be disposed adjacent distal end 222 of housing 202 and may be disposed within and extend through opening 219 of housing 202. Plate 218 may be disposed within housing 202 adjacent proximal end 220. In some embodiments, biasing element 216 is configured to couple knife 204 to plate 218.

In some embodiments, housing 202 may include opening 219 located at distal end 222. Opening 219 may allow knife 204 and insulator 210 to selectively extend away from and retract into housing 202 along central axis 205. For example, knife 204 and insulator 210 may be disposed within interior 226 of housing 202 along central axis 205 and may be configured to extend distally through opening 219. For example, knife 204 may have an extended position and a retracted position. In the extended position (FIG. 5), knife 204 may be extended distally from opening 219 along central axis 205 and in the retracted position (FIGS. 3-4), knife 204 may be retracted proximally towards proximal end 220 along central axis 205. In some embodiments, insulator 210 has an extended insulator position and a retracted insulator position. In the extended insulator position (FIG. 5), insulator 210 may be extended distally from opening 219 along central axis 205 and in the retracted position (FIG. 3), insulator 210 may be retracted proximally towards proximal end 220 along central axis 205 and may be disposed within housing 202.

In some embodiments, housing 202 is comprised of polytetrafluoroethylene (PTFE). However, housing 202 may be comprised of other materials such as polymers, copolymers, rubber, or vinyl. Housing 202 may be comprised of a biocompatible material. In some embodiments, housing 202 is comprised of a non-conductive material. Housing 202 may have an inner diameter between approximately 1.5 mm and approximately 3.0 mm, an outer diameter between approximately 1.5 mm and 3.5 mm, a wall thickness between approximately 0.05 mm and 0.5 mm, and a length between approximately 500 mm and 3000 mm. In some embodiments, housing 202 is comprised of PTFE having a thickness of approximately 0.45 mm. However, housing 202 may have a thickness between 0.1 mm and 0.5 mm. In some embodiments, housing 202 may be sized and shaped to be any length desired. For example, housing 202 may be longer to allow endoscopic surgical tool 200 to travel deeper into the GI tract for the excision of tissues or tumors within deeper portions of the GI tract.

In some embodiments, housing 202 is generally flexible to allow endoscopic surgical tool 200 to navigate the GI tract. Housing 202 may be comprised of a single sheath of non-rigid material allowing endoscopic surgical tool 200 to flex and bend around the curvatures of the GI tract. For example, housing 202 may be comprised of a flexible material forming a single sheath. However, housing 202 may be comprised of more than one sheath of material. In some embodiments, housing 202 is coupled to an actuator (not shown) to allow a user or surgeon to control endoscopic surgical tool 200. The actuator may be configured to extend and retract knife 204 and insulator 210. For example, the actuator may be configured to extend one or both of knife 204 and insulator 210, and lock knife 204 and insulator 210 into a desired position.

Referring to FIGS. 3 and 4, endoscopic surgical tool 200 may include knife 204 disposed within housing 202 along central axis 205. In practice, knife 204 is utilized when endoscopic surgical tool 200 is in the needle-shaped knife configuration (FIG. 3) or the knife with an insulator at the tip configuration (FIG. 5). Knife 204 may be used to cut/cauterize desired tissue and/or tumors. For example, knife 204 may be used to cauterize a tumor found along the GI tract by placing knife 204 adjacent to the tumor and cauterizing the tumor such that it may be peeled off and removed from the GI tract. Endoscopic surgical tool 200 may utilize cauterization to prevent bleeding and hemorrhaging within the GI tract. However, knife 204 may be configured to only cut tissue without cauterizing.

Referring to FIGS. 3 and 5, knife 204 may include cutting surface 207, distal portion 211, and tip 206. Tip 206 may be disposed on the distal end of distal portion 211 of knife 204 and may have a length between approximately 0.25 mm and 2.5 mm. Distal portion 211 may be disposed adjacent tip 206 and may be disposed between tip 206 and cutting surface 207. Cutting surface 207 may be disposed adjacent distal portion 211. Distal portion 211 of knife 204 may be used when endoscopic surgical tool 200 is in the needle-shaped knife configuration. When endoscopic surgical tool 200 is in the needle-shaped knife configuration, insulator 210 may remain disposed within housing 202 and distal portion 211 may extend away from insulator 210 and housing 202 through aperture 208 of insulator 210. Distal portion 211 may extend away from insulator 210 and housing 202 such that tip 206 and distal portion 211 are exposed, which allows distal portion 211 to contact and cut/cauterize the desired tissue. In the needle-shaped knife configuration, cutting surface 207 may remain disposed within insulator 210 and housing 202 while distal portion 211 and tip 206 are extended out of housing 202. In the knife with an insulator at the tip configuration, tip 206 and distal portion 211 may be disposed within insulator 210, which may be extended away from opening 219 and housing 202. Further, in the knife with an insulator at the tip configuration, cutting surface 207 may be exposed to allow cutting surface 207 to contact and cut/cauterize the desired tissue.

Referring to FIGS. 3-5, in some embodiments, cutting surface 207 is connected to a distal end of insulator 210. Cutting surface 207 may include rod 212, which may be surrounded by cutting edges 214a, 214b. Cutting edges 214a, 214b may include blades, wire, sharp corners, conductive material for cauterization, or other surfaces that are configured to cut through tissue. Rod 212 may be disposed along central axis 205 of housing. Cutting edges 214a, 214b may completely surround rod 212 along the circumference of rod 212 such that cutting edges 214a and 214b form a cylinder around rod 212 to form cutting surface 207. Cutting edges 214a, 214b may completely surround rod 212 to form a smooth and clean cutting and cauterizing surface around the perimeter or circumference of cutting surface 207. In some embodiments, cutting edges 214a, 214b may be coupled together circumferentially around rod 212. However, cutting surface 207 may include a single unitary cutting edge that surrounds rod 212. Cutting edges 214a, 214b may be coupled or a unitary piece such that only one of cutting edge 214a or 214b needs to be coupled to a wire providing electrical current to cutting surface 207 and/or knife 204. In some embodiments, cutting edge 214a of cutting surface 207 has a length greater than cutting edge 214b of cutting surface 207. For example, cutting edge 214a may extend fully down a majority of the length of housing 202 and through plate 218, whereas cutting edge 214b may only extend partially down the length of housing 202 and terminate prior to plate 218.

In some embodiments, cutting surface 207 includes more than two cutting edges. For example, cutting surface 207 may include three, four, five, six, or greater than six cutting edges. In some embodiments where cutting surface 207 includes more than two cutting edges, each cutting edge may have a portion adjacent to distal end 222 that has a width greater than a portion adjacent proximal end 220. Each cutting edge 214a, 214b having a wider portion adjacent distal end 222 compared to a thinner portion adjacent proximal end 220 allows cutting surface 207 to have a continuous circumference preventing gaps along the circumference or perimeter of cutting surface 207.

In some embodiments, cutting edge 214a extends through plate 218 to couple to a power source for providing electrical current to cutting edge 214a and/or cutting edge 214b. For example, cutting edge 214a may extend through plate 218 to couple to a power source and cutting edge 214a may be electrically coupled to or in contact with cutting edge 214b such that cutting edge 214b is also coupled to the power source. In some embodiments, cutting edges 214a, 214b are comprised of a conductive material to allow knife 204 to cauterize tissue. In some embodiments, tip 206 is an electrode disposed at the distal end of knife 204 to allow high-frequency electrical current to flow through knife 204 allowing knife 204 to be used for cauterizing.

In a preferred embodiment, knife 204 is comprised of stainless steel. For example, rod 212 and cutting edges 214a, 214b, may be comprised of stainless steel. However, knife 204 may be comprised of other conductive materials. In some embodiments, knife 204 is configured to extend out of housing 202 and retract into housing 202 through aperture 208 of insulator 210, which may be disposed within housing 202. For example, distal portion 211 of knife 204 may be configured to partially extend out of housing 202 through insulator 210 (FIG. 3), distal portion 211 and cutting surface 207 may fully extend out of housing 202 with insulator 210 (FIG. 5), and distal portion 211 and cutting surface 207 may retract into insulator 210 when insulator is disposed adjacent to opening 219 of housing 202 (FIG. 4). Distal portion 211 of knife 204 may partially extend out of housing 202 such that endoscopic surgical tool 200 is in the needle-shaped knife configuration (FIG. 3) allowing distal portion 211 to contact the desired tissue. For example, knife 204 may extend partially allowing distal portion 211 and tip 206 of knife 204 to be exposed to the desired tissue. Distal portion 211 of knife 204 may partially extending out of housing 202 while insulator 210 remains disposed within housing 202.

In practice, an operator or surgeon may utilize an actuator (not shown) to control the extension of knife 204. For example, an operator or surgeon may engage the actuator to extend knife 204 during use of endoscopic surgical tool 200 in the needle-shaped knife configuration such that only distal portion 211 and tip 206 extended away from opening 219 and housing 202 and thus are exposed. In some embodiments, tip 206 of knife 204 extends between 1.5 mm and 2 mm away from insulator 210 in the needle-shaped knife configuration (FIG. 3), resulting in distal portion 211 being between 1.5 mm and 2 mm. For example, in the needle-shaped knife configuration, knife 204 may only extend such that distal portion 211 and tip 206 are exposed, with the cutting surface 207 and the remainder of knife 204 being disposed within insulator 210, which is disposed within housing 202. The distance between tip 206 and insulator 210, and thus the length of distal portion 211, when in the needle-shaped knife configuration may be between 0.5 mm and 3 mm, 0.75 mm and 2.5 mm, and 1 mm and 2 mm. In some embodiments, the length of insulator 210 is between 3 mm and 4 mm. However, may be between 2 mm and 5 mm, 2.5 mm and 4.5 mm, or 3 mm and 3.5 mm.

In some embodiments, knife 204 is disposed through insulator 210. Insulator 210 may include aperture 208 defined by an opening and central bore 215 disposed along central axis 205 and knife 204 may be configured to travel through central bore 215 and in and out of aperture 208. For example, knife 204 may be configured to pass through aperture 208 and central bore 215 when extending out of and retracting into housing 202. In practice, distal portion 211 of knife 204 may partially extend out of housing 202 and insulator 210 when in the needle-shaped knife configuration (FIG. 3). In some embodiments, insulator 210 has a maximum diameter of approximately 5 mm. However, insulator 210 may have a maximum diameter between 0.5 mm and 5 mm, 1 mm and 3.5 mm, or 1.5 mm and 3 mm. Further, insulator 210 may have a length of approximately 5 mm. However, insulator 210 may have a length between 0.5 mm and 5 mm, 0.75 mm and 3 mm, 1 mm and 2.5 mm, or 1.5 mm and 2 mm. In some embodiments, insulator 210 is comprised of a non-conductive material, such as ceramic. However, insulator 210 may be comprised of PTFE, polymers, co-polymers, rubber, or other non-conductive materials. Insulator 210 may be made of insulating material or may be made of conductive or non-conductive material with an insulating coating. In some embodiments, an exterior surface of insulator 210 may be substantially smooth to allow insulator 210 to contact tissue without disrupting the tissue or causing harm to the tissue.

In some embodiments, insulator 210 includes recess 224. Recess 224 may be sized and shaped to receive tip 206 when knife 204 is in the retracted position or when insulator 210 is extend distally away from opening 219 along knife 204. For example, insulator 210 may extend distally while knife 204 is locked in a fixed position resulting in insulator 210 traveling distally along knife 204 and/or along central axis 205. Recess 224 may be disposed at a distal end of insulator 210 and may extend proximally from the distal end of insulator 210 along central axis 205. In some embodiments, knife 204 may be in the retracted position and disposed within insulator 210, which may be initially disposed within housing 202. For example, tip 206 may be disposed within recess 224 such that when insulator 210 is extended distally, tip 206 and knife 204 also extend distally.

Referring to FIGS. 3-5, recess 224 may have a radius greater than the radius of tip 206 and a depth greater than length of tip 206. For example, tip 206 may have a radius between approximately 0.25 mm and 1.5 mm and a length between approximately 0.10 mm and 0.5 mm. In some embodiments, recess 224 has a depth of approximately 0.5 mm or more. For example, recess 224 may have a depth between 0.2 mm and 2.5 mm, 0.5 mm and 2 mm, or 1 mm and 1.5 mm, or greater than 0.5 mm. Recess 224 may be configured to prevent knife 204 from retracting further into housing 202 by preventing tip 206 from moving proximally once tip 206 is disposed within recess 224. For example, recess 224 may have a diameter greater than central bore 215, thereby preventing tip 206 from retracting proximally past recess 224. In some embodiments, tip 206 of knife 204 is disposed within recess 224 and insulator 210 extends distally such that insulator 210 pushes tip 206 and knife 204 out distally. For example, extension of insulator 210 may result in the extension of knife 204 when tip 206 of knife 204 is disposed within recess 224 due to insulator 210 pushing against tip 206 of knife 204. Tip 206 being disposed within recess 224 may result in distal portion 211 being disposed with central bore 215. For example, in the knife with an insulator at the tip configuration, when insulator 210 extends distally away from housing 202, tip 206 may be disposed within recess 224 and distal portion 211 may be disposed within central bore 215 of insulator 210 resulting in cutting surface 207 being exposed and able to contact the desired tissue.

Figure 6B:
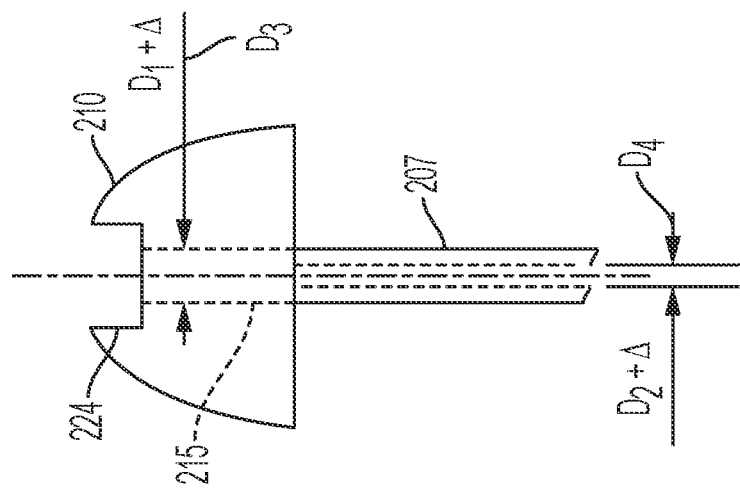
FIG. 6B is a side view of an exemplary insulator and cutting surface of the endoscopic tool of FIGS. 3-5.
Figure 6A:
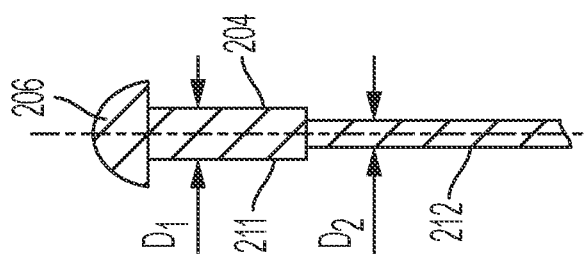
FIG. 6A is a side view of an exemplary knife of the endoscopic tool of FIGS. 3-5.

Referring to FIGS. 6A and 6B, insulator 210 may be sized and shaped to house a portion of knife 204. For example, distal portion 211 of knife 204 may be disposed within and extend through central bore 215 of insulator 210. In some embodiments, distal portion 211 has diameter $D_1$ and rod 212 has diameter $D_2$. Diameter $D_1$ may be between approximately 0.2 mm and 0.8 mm and diameter $D_2$ may be between approximately 0.05 mm and 0.5 mm. Diameter $D_1$ may be greater than diameter $D_2$. Diameter $D_1$ may be approximately 0.4 mm. However, diameter $D_1$ may be between 0.1 mm and 2 mm, 0.3 mm and 0.6 mm, or 0.5 mm and 1 mm. In some embodiments, diameter $D_1$ of distal portion 211 is the same as the diameter of cutting surface 207. In some embodiments, diameter $D_2$ of rod 212 plus the thickness of cutting edges 214a, 214b are equal to diameter $D_1$. Referring to FIG. 6B, central bore 215 may have diameter $D_3$, which may be greater than diameter $D_1$. For example, diameter $D_3$ may be greater than diameter $D_1$ by delta Δ. Diameter $D_3$ may be between approximately 0.25 mm and 0.75 mm. In some embodiments, endoscopic surgical tool 200 includes diameter $D_4$. Diameter $D_4$ may be equal to the diameter $D_2$ plus delta Δ to ensure that there is sufficient space for cutting surface 207 to longitudinally move through central bore 215 along central axis 205. For example, diameter $D_4$ may be less than diameter $D_3$ of central bore 215. In some embodiments, diameter $D_4$ is between approximately 0.05 mm and 0.5 mm. In some embodiments, delta Δ is between approximately 0.01 mm and 0.05 mm. Delta Δ may allow clearance between cutting surface 207 and the interior of central bore 215 for the addition of, for example, a bonding agent, such as glue or an adhesive. and at its natural length when insulator 210 is in the retracted position. Biasing element 216 may become extended when insulator 210 is in the extended insulator position. In the extended position, biasing element 216 provides a biasing force to knife 204 and tip 206, pulling knife 204 and tip 206 towards proximal end 220.

In alternative embodiments, rod 212 may extend through plate 218 and biasing element 216 may be coupled to proximal side 243 of plate 218 such that biasing element 216 couples to rod 212 adjacent proximal side 243 of plate 218. For example, biasing element 216 may be coupled to proximal side 243 of plate 218 such that biasing element 216 extends proximal end 220 and is configured to push rod 212 towards proximal end 220. Biasing element 216 being coupled to proximal side 243 of plate 218 and configured to push rod 212 towards proximal end 220 may prevent knife 204 and tip 206 from inadvertently extending through insulator 210.

Referring to FIGS. 3-5, endoscopic surgical tool 200 may be configured to be in a needle-shaped knife configuration (FIG. 3) and a knife with an insulator at the tip configuration (FIG. 4). Endoscopic surgical tool 200 may be in the needle-shaped knife configuration when distal portion 211 and tip 206 of knife 204 are extended out of insulator 210 and away from opening 219. For example, the needle-shaped knife configuration may be when knife 204 is distally extended from opening 219, but insulator 210 is still disposed within housing 202. In the needle-shaped knife configuration, distal portion 211 of knife 204 is prevented from retracting into housing 202 via an actuator (not shown). In practice, to go from the needle-shaped knife configuration (FIG. 3) to the knife with an insulator at the tip configuration (FIG. 5), an actuator (not shown) is used to extend insulator 210. Insulator 210 may extend away from opening 219 such that tip 206 of knife 204 becomes disposed within recess 224 of insulator as shown in FIG. 4. Tip 206 may contact and become disposed within recess 224 because as insulator 210 extends away from opening 219 and housing 202, distal portion 211 of knife 204 is not extending or retracting resulting in recess 224 of insulator 210 contacting tip 206. As insulator 210 continues to extend distally away from opening 219, insulator 210 pushes tip 206 distally away from opening 219 resulting in knife 204 extending distally along with insulator 210 as shown in FIG. 5.

In some embodiments, biasing element 216 applies a biasing force on tip 206 and knife 204 causing tip 206 to remain in recess 224 as insulator 210 extends away from opening 219 and housing 202. For example, the biasing force of biasing element 216 pulling tip 206 towards proximal end 220 acts opposite the force of insulator 210 extending tip 206 distally away from opening 219. In some embodiments, the biasing force of biasing element 216 is less than the force of insulator 210 on tip 206 as insulator 210 extends distally allowing insulator 210 to extend distally while tip 206 is still being biased towards proximal end 220. Insulator 210 may be locked into an extended position during use and the biasing force of biasing element 216 on tip 206 of knife 204 results in tip 206 being pulled into recess 224 thereby preventing inadvertent protrusion of tip 206 and knife 204.

In some embodiments, when insulator 210 extends away from opening 219 to be in a locked and extended position, biasing element 216, which is coupled to plate 218 and rod 212, becomes extended. The extension of biasing element 216 causes a biasing force that pulls rod 212 toward proximal end 220. The biasing force of biasing element 216 pulling rod 212 towards proximal end 220 results in tip 206 of knife 204 remaining within recess 224.

Referring to FIGS. 3-5 and 7A-7B, biasing element 216 may be coupled to plate 218. Plate 218 may be comprised of hard or rigid material, such as metal, steel, resin, or a polymer. Plate 218 may be circular and may be disposed within interior 226 of housing 202. However, plate 218 may be rectangular, oval, square, triangular, semi-circular, or any other shape desired. In some embodiments, plate 218 has a diameter substantially the same as the inner diameter of housing 202. In some embodiments, plate 218 extends around the entire inner circumference of housing 202 and may have a diameter less than the outer diameter of housing 202. However, plate 218 may only extend around a portion of the inner circumference of housing 202. For example, plate 218 may only extend between 10° and 345°, 45° and 300°, 90° and 270°, 120° and 225°, or 180° and 200°. Plate 218 may be disposed within housing 202 such that plate 218 is substantially perpendicular to central axis 205. In some embodiments, plate 218 has a thickness between approximately 0.5 mm and 5 mm. The thickness of plate 218 may be sized to not interfere with the bending of endoscopic surgical tool 200. In some embodiments, plate 218 is configured to secure and stabilize cutting surface 207, including rod 212 and cutting edges 214a, 214b, thereby preventing inadvertent lateral movement.

In some embodiments, plate 218 includes plate opening or plate aperture 230. Plate 218 may include more than one plate opening 230. For example, plate 218 may include two, three, four, five, or six plate openings 230 disposed about plate 218. In some embodiments, plate 218 may include more than one plate opening 230 to allow multiple cutting edges to extend through plate 218. In some embodiments, endoscopic surgical tool 200 includes a plurality of cutting edges and one or more of the cutting edges may be disposed through the more than one plate openings 230. In some embodiments, plate 218 may have more than one plate opening 230 and each plate opening 230 may be equidistant from an adjacent plate opening 230.

In some embodiments, plate opening or plate aperture 230 is sized and shaped to allow one or more of cutting edges 214a, 214b to pass through plate 218. In a preferred embodiment, plate 218 only allows one of cutting edges 214a or 214b to pass through in order to allow biasing element 216 to couple to plate 218. For example, allowing both cutting edges 214a, 214b, each spanning halfway around plate 218, to pass through plate 218 would result in a hole at point 231 along central axis 205, where biasing element 216 couples to plate 218. Therefore, to allow biasing element 216 to couple to plate 218 at point 231, plate 218 only includes one plate opening 230 configured to allow one of cutting edges 214a or 214b to pass through plate 218. However, plate 218 may include multiple plate openings 230 configured to allow multiple cutting edges to be disposed through plate, while still maintaining point 231 for coupling of biasing element 216 to plate 218.

In some embodiments, cutting edge 214a has a length greater than cutting edge 214b to allow cutting edge 214a to extend through plate opening 230 of plate 218. For example, cutting edge 214a may have a length between approximately 2 mm and approximately 5 mm and cutting edge 214b may have a length between approximately 4 mm and approximately 10 mm. Plate opening 230 may be sized and shaped to allow cutting edge 214a or 214b to pass through. For example, plate opening 230 may be semi-circular in shape. However, plate opening 230 may be rectangular, triangular, oval, or any other shaped desired. In some embodiments, plate opening 230 is disposed on plate 218 offset from central axis 205. In some embodiments, plate opening 230 extends around plate 218 less than 360°. For example, plate opening 230 may extend around plate 218 between 10° and 345°, 45° and 300°, 90° and 270°, 120° and 225°, or 180° and 200°. In some embodiments, plate opening 230 extends around plate 218 between 30° and 330°. Plate opening 230 may have a length of sized and shaped to receive one of cutting edge 214a or 214b. In some embodiments, plate 218 has a length between approximately 0.01 mm and 0.05 mm.

Figure 7B:
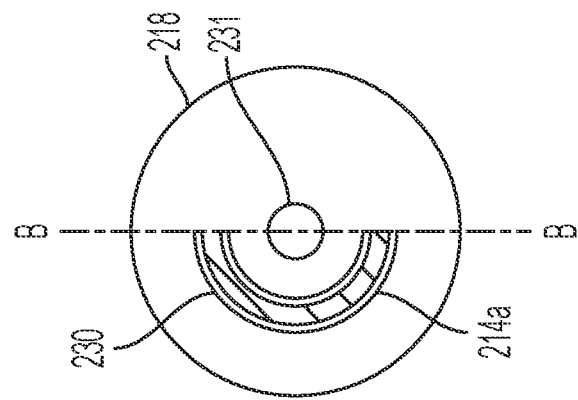
FIG. 7B is a cross-sectional view of the endoscopic surgical tool of FIG. 5 taken across the B-B axis.
Figure 7A:
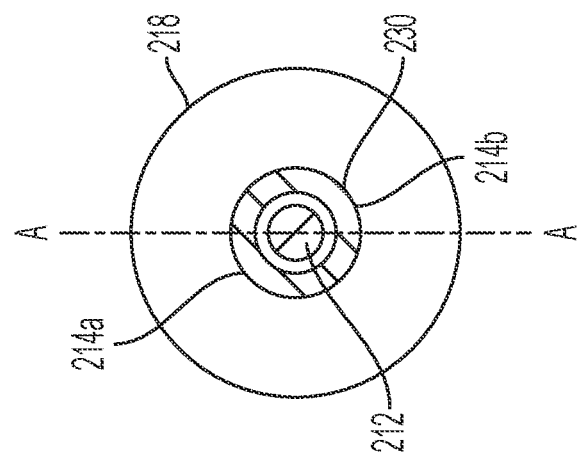
FIG. 7A is a cross-sectional view of the endoscopic surgical tool of FIG. 5 taken across the A-A axis.

Referring to FIGS. 7A and 7B, cross-sectional views of endoscopic surgical tool 200 are shown. FIG. 7A shows a cross-sectional view of plate 218 taken about the A-A axis of FIG. 5 and FIG. 7B shows a cross-sectional view of plate 218 taken about the B-B axis of FIG. 5. The A-A axis is adjacent to opening 219 and distal end 222, and the B-B axis is adjacent to point 231 and proximal end 220, where biasing element 216 couples to plate 218. At the A-A axis, both cutting edges 214a and 214b are present. However, at the B-B axis and adjacent point 231, cutting edge 214a is no longer present to allow biasing element 216 to couple to point 231. If both cutting edges 214a and 214b passed through plate opening 230, then cutting edges 214a and 214b would create a hole at point 231 due to cutting edges 214a and 214b creating a cylinder around rod 212. This would result in biasing element 216 not being able to couple to plate 218 at point 231.

Figure 8:
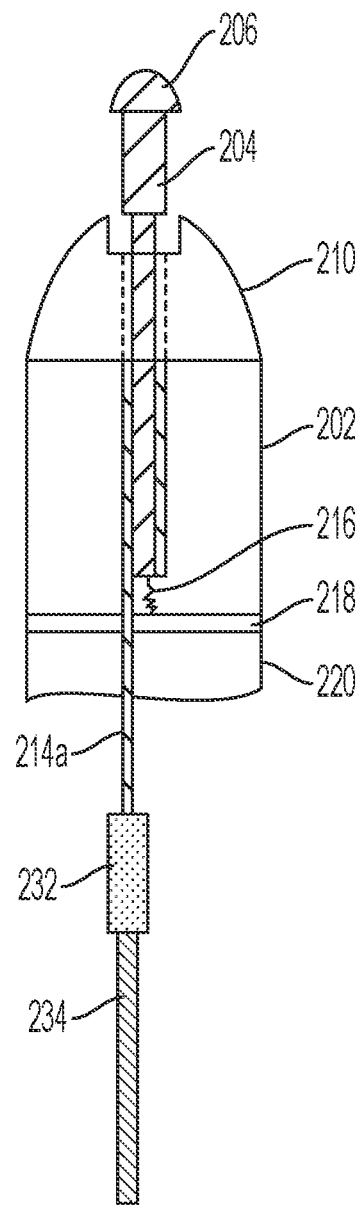
FIG. 8 is a cross-sectional view of the endoscopic surgical tool of FIG. 3 shown with an operation wire.

Referring to FIG. 8, endoscopic surgical tool 200 may include conducting wire to provide electrical current to knife 204. In one embodiment, shown in FIG. 8, endoscopic surgical tool 200 may include a single operation wire 234. Operation wire 234 may be welded to cutting edge 214a via welding spot 232. Operation wire 234 may be configured to supple electrical current from a power source (not shown) through cutting edge 214a to cutting edge 214b to allow current to flow through knife 204 enabling knife 204 to cut and cauterize tissue. In some embodiments, cutting surface 207 is connected to a distal end of operation wire 234. Operation wire 234 may be configured to provide electrical current to knife 204 regardless of endoscopic surgical tool 200 being in the needle-shaped knife configuration or the knife with an insulator at the tip configuration.

Figure 9:
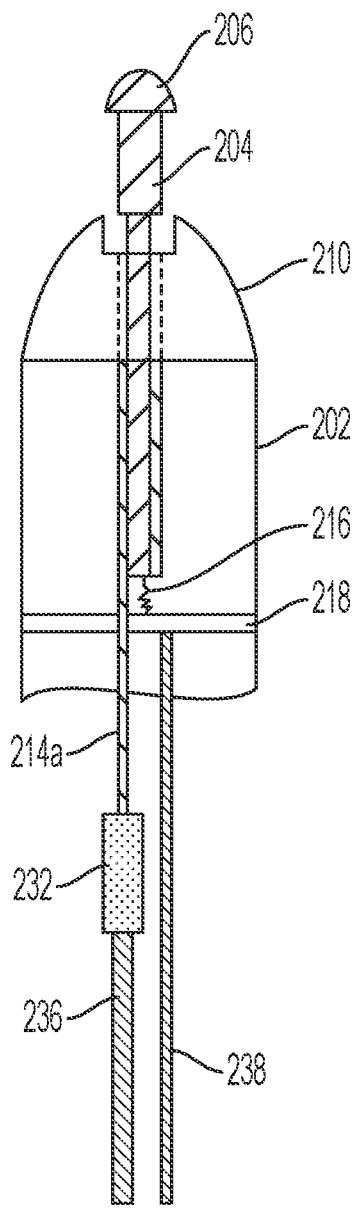
FIG. 9 is a cross-sectional view of the endoscopic surgical tool of FIG. 8 shown with an additional operation wire.

In some embodiments, shown in FIG. 9, endoscopic surgical tool 200 may include more than one operation wire. For example, endoscopic surgical tool 200 may include operation wire 236 and operation wire 238. Operation wire 236 may be coupled to cutting edge 214a to provide electrical current from a power source (not shown) through cutting edge 214a to cutting surface 207. Further, operation wire 238 may be coupled to plate 218 and may be configured to provide electrical current to one or more of cutting surface 207 and distal portion 211 via, for example, biasing element 216. However, endoscopic surgical tool 200 may include as many operation wires as desired. For example, endoscopic surgical tool 200 may include three, four, five, six, seven, eight, or more than eight operation wires.

Referring to FIGS. 3 and 10A-13B, endoscopic surgical tool 200 may include a second insulator 240. The second insulator 240 may include an inner surface 240a and an outer surface 240b, and may have proximal end 240c and a distal end 240d. The proximal end 240c of the second insulator 240 may be inside the housing 202. The distal end 240d of the second insulator 240 may be adjacent to or flush with the distal end 222 of the housing 202. The inner surface 240a of the second insulator 240 may have a cross-section having a narrower diameter at the distal end 240d than at the proximal end 240c.

The endoscopic surgical tool 200 may also include a connection element 242, and one or more protrusions 244. The connection element 242 may surround the biasing element 216, and may be insertable into the inner surface 240a of the second insulator 240.

Figure 10C:
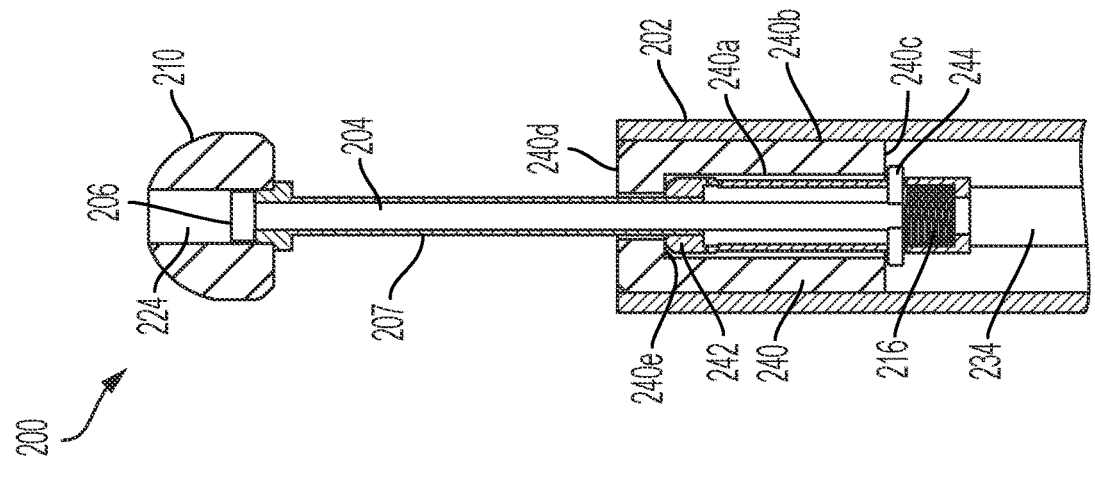
FIG. 10C is a cross-sectional view of the endoscopic surgical tool of FIG. 3 shown in a an insulator state.
Figure 10B:
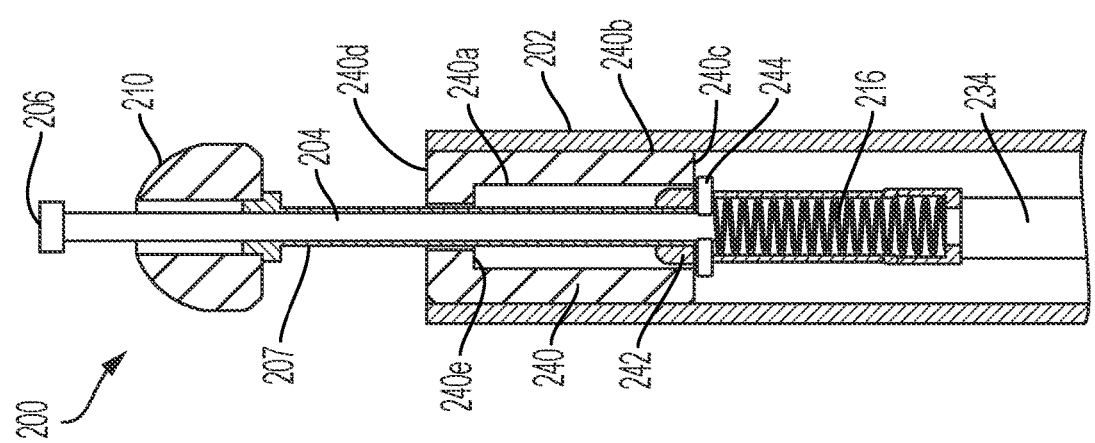
FIG. 10B is a cross-sectional view of the endoscopic surgical tool of FIG. 3 shown in an intermediate state.
Figure 10A:
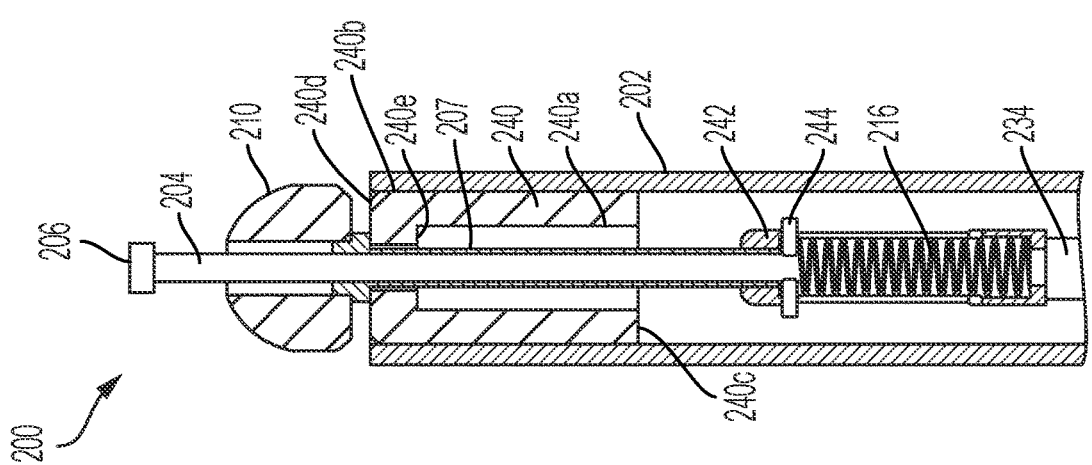
FIG. 10A is a cross-sectional view of the endoscopic surgical tool of FIG. 3 shown in a knife state.

The configurations of FIGS. 10A-13B allow switching between the needle-shaped knife configuration ("knife state") described above and a configuration having the knife 204 with an insulator 210 at the tip 206 ("insulator state") by advancing and retreating the operation wire 234. FIG. 10A shows the knife state, in which the operation wire 234 is fully retracted and the biasing element 216 is in an equilibrium state. FIG. 10B shows an "intermediate state" between the knife state and the insulator state. FIG. 10C shows the insulator state in which the insulator is at the tip. In the insulator state shown in FIG. 10C, the operation wire 234 is fully extended and the biasing element 216 is in a compressed state.

Figure 11A:
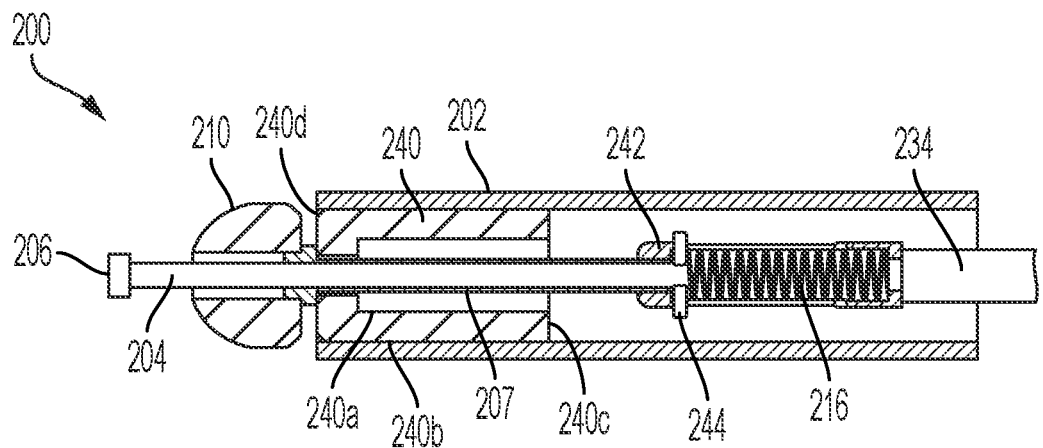
FIG. 11A is a cross-sectional view of the endoscopic surgical tool of FIG. 10A.
Figure 11B:
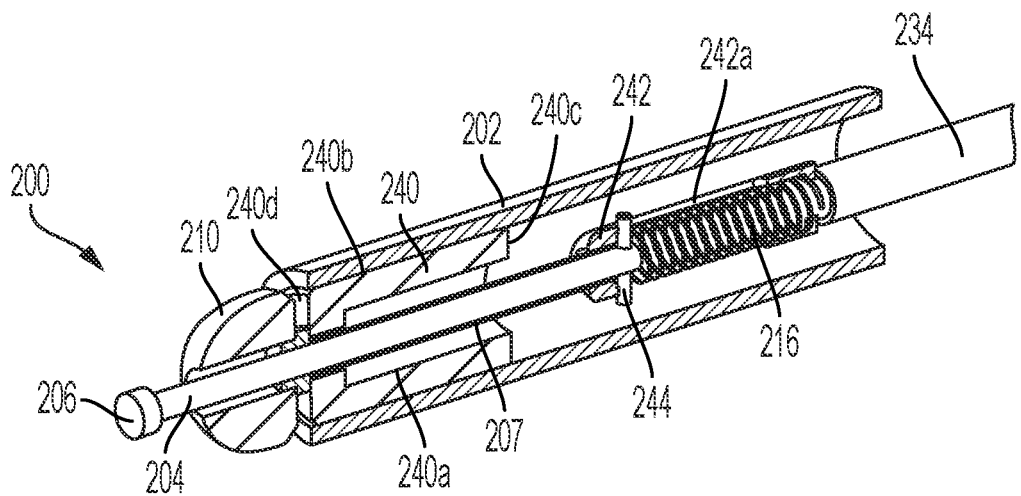
FIG. 11B is an opened perspective view of the endoscopic surgical tool of FIG. 10A.

In the knife state shown in the examples of FIGS. 10A and 11A-11B, the treatment tool 200 can be used in the needle-shaped knife configuration. The insulator 210 may be connected to a distal end of the cutting surface 207. A proximal end of the cutting surface 207 may be connected to the connection element 242. The connection element 242 may be connected to the operating wire 234. The connection element 242 may include one or more elongated openings 242a corresponding to the one or more protrusions 244. An interior of the connection element 242 may accommodate the biasing element 216. A distal end of the biasing element 216 may be connected to an interior of the connection element 244.

Figure 12A:
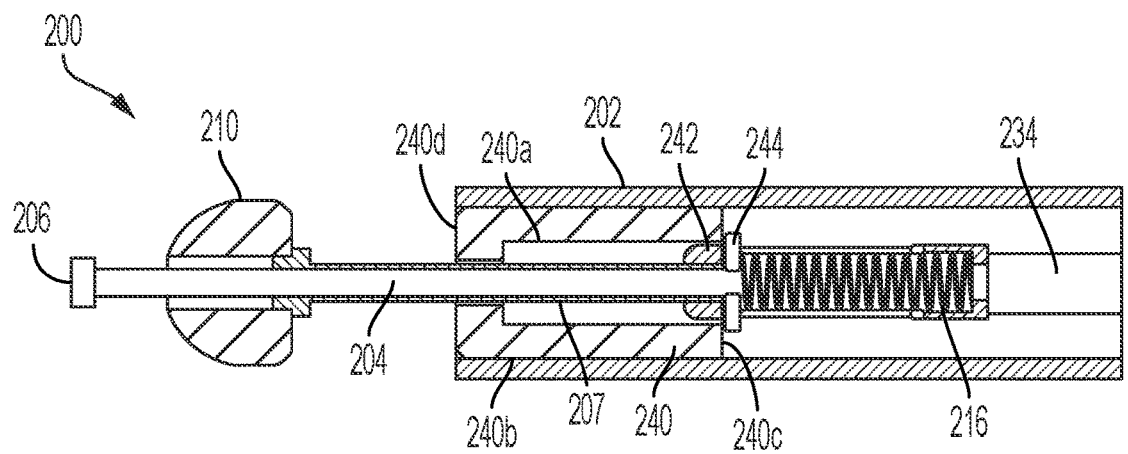
FIG. 12A is a cross-sectional view of the endoscopic surgical tool of FIG. 10B.
Figure 12B:
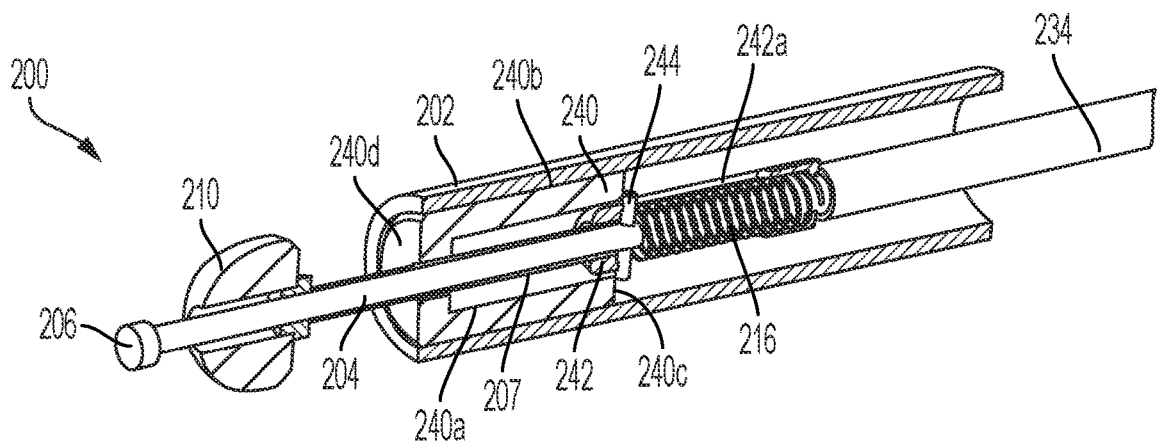
FIG. 12B is an opened perspective view of the endoscopic surgical tool of FIG. 10B.

In the intermediate state shown in the examples of FIGS. 10B and 12A-12B, the operating wire 234 may be partially advanced/retracted. The biasing element 216 may be in an equilibrium state. The one or more protrusions 244 may be in contact with a proximal end 240c of the second insulator 240. The insulator 210 may be separated from the distal end 240d of the second insulator 240. The examples of FIGS. 10B and 12A-12B show that the operating wire 234 may be advanced until the one or more protrusions 244 contact the proximal end 240c of the second insulator 240. A diameter of a proximal end of a through hole in the second insulator 240, e.g., a diameter of the inner surface 240a adjacent the proximal end 240c of the second insulator 240, may be smaller than the one or more protrusions 244, providing an upper inner barrier 240e. Thus, when the operating wire 234 is advanced, the one or more protrusions 244 may not advance further after the one or more protrusions 244 contact the proximal end 240c of the second insulator 240. Therefore, the knife 204 may not advance any further. However, the connection element 242 may advance further by the one or more protrusions 244 moving through the openings 242a provided in the connection element 242.

Figure 13A:
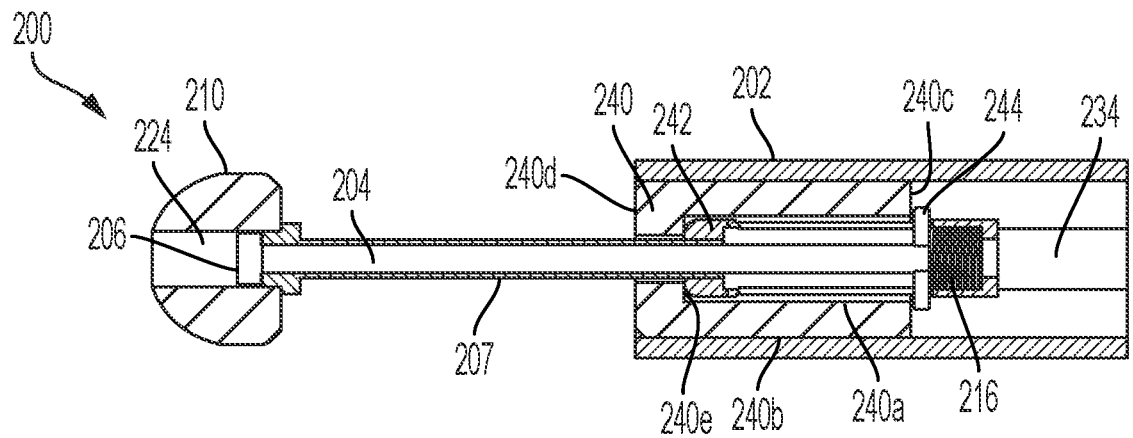
FIG. 13A is a cross-sectional view of the endoscopic surgical tool of FIG. 10C.
Figure 13B:
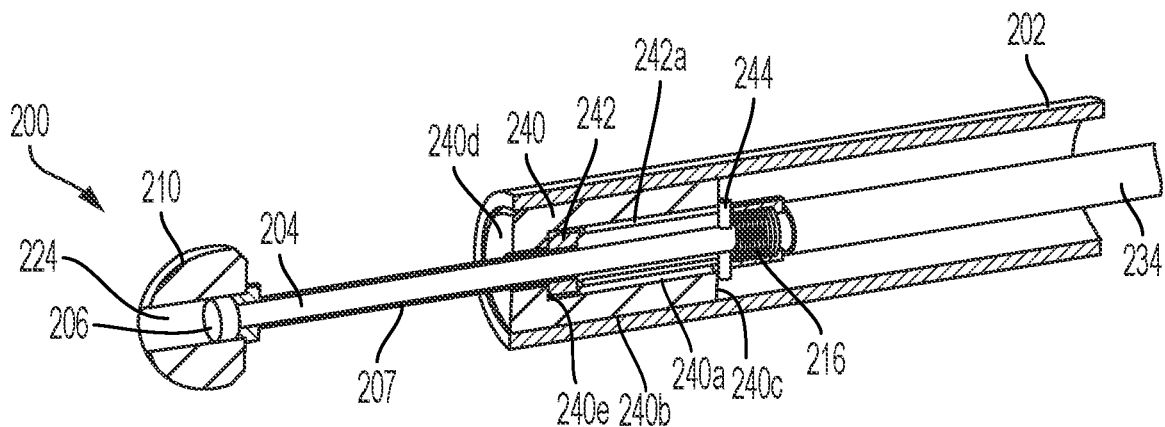
FIG. 13B is an opened perspective view of the endoscopic surgical tool of FIG. 10C.

If the operation wire 234 is moved forward from the intermediate state shown in FIGS. 10B and 12A-12B, the insulator state can be achieved, as shown in the examples of FIGS. 10C and 13A-13B. When the operating wire 234 is advanced, the connection element may be advanced until the distal end of the connection element 242 contacts a narrowing of the inner surface 240a of the second insulator 240 near the distal end 240d of the second insulator 240 at the upper inner barrier 240e. The contact at the upper inner barrier 240e stops the connection element 242 from being able to be pushed out of the distal end 240d of the second insulator 240, while the cutting edge 207 and the insulator 210 may continue to be advanced. When the connection element 242 is advanced, the cutting edge 207 and the insulator may also be advanced until the biasing element 216 is in a compressed state. Thus, the insulator 210 may be advanced further than the knife 204. As such, the tip 206 may be enclosed within and surrounded laterally by the insulator 210 within the recess 224. In the insulation state shown in FIGS. 10C and 13A-13B, the treatment tool 200 can be used as the knife 204 with an insulator 210 at the tip 206.

The treatment tool 200 can be changed from being in the insulation state to the knife state by reversing the operations shown in FIGS. 10A-13B. The reverse operation may be achieved by retracting the operation wire 234 at least until the operation wire 234 is at an equilibrium length. Thus, the treatment tool 200 may be moved from the insulation state to the intermediate state, and then to the knife state.

It will be appreciated by those skilled in the art that changes could be made to the exemplary embodiments shown and described above without departing from the broad inventive concepts thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and various features of the disclosed embodiments may be combined. The words "proximal", "distal", "upper" and "lower" designate directions in the drawings to which reference is made. Unless specifically set forth herein, the terms "a", "an" and "the" are not limited to one element but instead should be read as meaning "at least one".

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

What is claimed is:

1. An endoscopic surgical tool, comprising:
   a housing having a first aperture extending along a longitudinal axis of the housing;
   a knife extending through the first aperture and having a pipe, wherein at least a part of the pipe is configured to protrude from the housing;
   a rod disposed inside the pipe, wherein the rod is configured to move along the longitudinal axis of the housing with respect to the pipe;
   a wire extending along the longitudinal axis of the housing, wherein the wire has a distal end and a proximal end;
   a connector coupling the distal end of the wire with the pipe; and
   a spring disposed between a proximal end of the rod and the connector, wherein the spring extends in the longitudinal axis of the housing.

2. The endoscopic surgical tool of claim 1, wherein the knife has an insulator coupled to the pipe.

3. The endoscopic surgical tool of claim 2, wherein the rod has an enlarged tip at a distal end of the rod, and wherein the part of the pipe configured to protrude from the housing extends from a distal end of the housing toward the enlarged tip.

4. The endoscopic surgical tool of claim 3, wherein the insulator includes a recess at a distal end thereof, and wherein the recess is sized and shaped to receive the enlarged tip.

5. The endoscopic surgical tool of claim 3, wherein the insulator has a first lumen, and wherein the enlarged tip is movable in the lumen in the longitudinal direction of the knife.

6. The endoscopic surgical tool of claim 5, wherein the housing has a second insulator at the distal end of the housing,
   wherein the second insulator has a second lumen, and
   wherein the pipe is movable in the second lumen in the longitudinal direction of the knife.

7. The endoscopic surgical tool of claim 6, wherein the enlarged tip is configured to be stored in the first lumen in case that the enlarged tip contacts with a distal end of the pipe.

8. The endoscopic surgical tool of claim 2, wherein the first aperture is sized and shaped to receive the insulator.

9. The endoscopic surgical tool of claim 8, wherein the knife has a retracted position and an extended position,
   wherein, in the extended position, the knife is extended distally from the first aperture, and, in the retracted position, the knife is retracted proximally with respect to the first aperture, and
   wherein the spring biases the knife toward the proximal end of the housing when the knife is in the extended position.

10. The endoscopic surgical tool of claim 1, wherein the rod has an enlarged tip at a distal end of the rod.

11. The endoscopic surgical tool of claim 10, wherein the pipe has a distal portion connected to the insulator, and wherein the distal portion of the pipe is disposed between the enlarged tip and the distal end of the pipe.

12. The endoscopic surgical tool of claim 1, wherein at least part of the connector is formed in a tubular shape, and wherein the spring is located inside the connector.

13. The endoscopic surgical tool of claim 1, wherein the knife is configured to move along the longitudinal axis of the housing with respect to the housing.

14. The endoscopic surgical tool of claim 1, wherein the housing includes a substantially flexible material.

15. The endoscopic surgical tool of claim 1, wherein the knife is an electrode.

16. The endoscopic surgical tool of claim 1, wherein the knife has an insulator coupled to the pipe,
   wherein the rod has an enlarged tip at a distal end of the rod, and
   wherein an outer circumference of the enlarged tip is covered by the insulator when the enlarged tip contacts with a distal end of the pipe.

17. An endoscopic surgical tool, comprising:
   a housing including a plate disposed proximate a proximal end and a first aperture defining an opening disposed proximate a distal end;
   an insulator disposed within the housing and including a central bore, a recess, and a second aperture, the insulator being configured to extend distally from the first aperture;
   a knife disposed within the first aperture and including a tip, the knife having a retracted position and an extended position, wherein, in the extended position, the knife is extended distally from the first aperture along the central axis, and, in the retracted position, the knife is retracted proximally towards the proximal end, the tip being sized and shaped to sit within the recess of the insulator; and
   a biasing element having a first end and a second end, the first end being coupled to the knife and the second end being coupled to the plate, the biasing element biasing the knife toward the retracted position when the knife is in the extended position.

18. An endoscopic surgical tool, comprising:
a housing including a single sheath of a substantially flexible material, the housing further including a plate disposed proximate a proximal end and an aperture defining an opening disposed proximate a distal end, the housing further including a central axis substantially perpendicular to the plate, the plate including a plate aperture;
an insulator disposed within the housing and including a central bore, a recess, and an insulator aperture, the insulator being configured to extend distally from the aperture along the central axis, the insulator having an extended insulator position and a retracted insulator position, the extended insulator position being when the insulator is extended distally from the aperture, and the retracted position being when the insulator is retracted proximally towards the proximal end;
a knife including a rod surrounded by a first cutting edge and a second cutting portion, the knife being disposed within the insulator aperture along the central axis, the knife including an electrode, and the knife having a retracted position and an extended position, wherein, in the extended position, the knife is extended distally from the aperture along the central axis, and, in the retracted position, the knife is retracted proximally towards the proximal end along the central axis, the electrode being sized and shaped to sit within the recess of the insulator, wherein the first cutting edge is disposed through the plate aperture and has a length greater than a length of the second cutting portion; and
a spring having a first end and a second end, the first end being coupled to the rod and the second end being coupled to the plate along the central axis, the spring biasing the knife toward the retracted position when the knife is in the extended position and the insulator is in the extended insulator position.

19. An endoscopic surgical tool, comprising:
a knife including:
a pipe having a cutting surface at an outer surface thereof, wherein the pipe is configured to move in a longitudinal direction of the knife, and
a rod inside the pipe, wherein the rod includes an enlarged tip and is configured to move in the longitudinal direction of the knife independently of the pipe;
a first insulator coupled to the pipe, the first insulator having a first lumen in which the enlarged tip is configured to move in the longitudinal direction of the knife; and
a second insulator coupled to the first insulator via the pipe, the second insulator having a second lumen in which the pipe is configured to move in the longitudinal direction of the knife,
wherein the enlarged tip is configured to be stored in the first lumen in case that the enlarged tip contacts with a distal end of the pipe.

20. The endoscopic surgical tool of claim 19, further comprising:
a biasing element coupled to both a proximal end of the rod and a proximal end of the pipe; and
a wire coupled to a proximal end of the biasing element, wherein, by actuating the wire, the biasing element is configured to stretch and compress in the longitudinal direction of the knife, and
wherein the pipe is configured to move in the longitudinal direction of the knife by the stretching and compressing of the biasing element.

* * * * *